United States Patent [19]

Bunin

[11] Patent Number: 5,346,481

[45] Date of Patent: Sep. 13, 1994

[54] VACCINE DELIVERY SYSTEM

[75] Inventor: Leonid Bunin, Woodbridge, N.J.

[73] Assignee: Merck & Co., Inc., Rahway, N.J.

[21] Appl. No.: 137,239

[22] Filed: Oct. 14, 1993

[51] Int. Cl.$^5$ ............................................. A61M 5/00
[52] U.S. Cl. ................................ 604/204; 604/187; 604/232
[58] Field of Search .............. 604/204, 203, 202, 201, 604/200, 187, 218, 232

[56] References Cited

U.S. PATENT DOCUMENTS

| 937,029 | 10/1909 | Strong | 604/204 |
|---|---|---|---|
| 2,805,662 | 9/1957 | Lawshe et al. | 604/204 |
| 2,890,698 | 6/1959 | Sloane | 604/204 |
| 3,089,489 | 5/1963 | Dunmire | 604/204 |

Primary Examiner—John D. Yasko
Attorney, Agent, or Firm—Hesna J. Pfeiffer; Joseph F. DiPrima

[57] ABSTRACT

A disposable vaccine delivery system containing a single dosage vaccine, having a compressible "hour-glass" shaped container portion filled with a needle, containing the vaccine, enclosed in a rigid clamp assembly having syringe-type activation means for compressing and expelling the vaccine contents into the human subject.

6 Claims, 2 Drawing Sheets

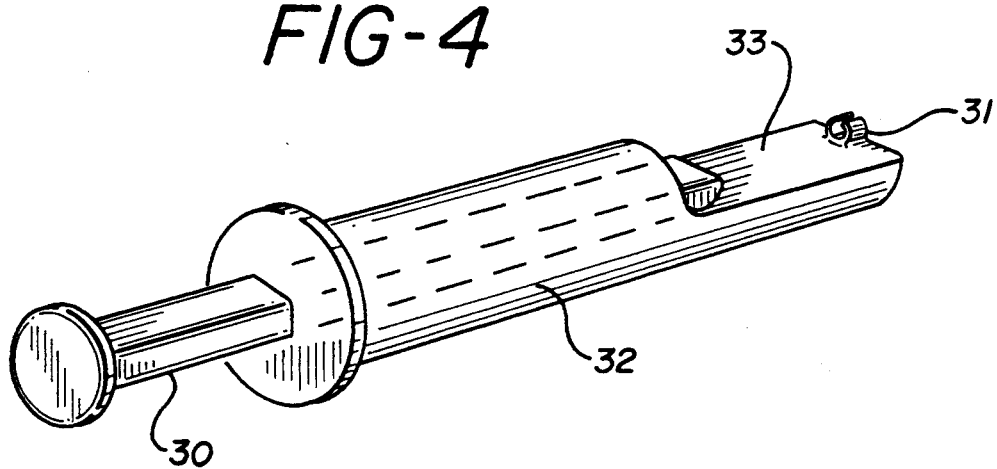
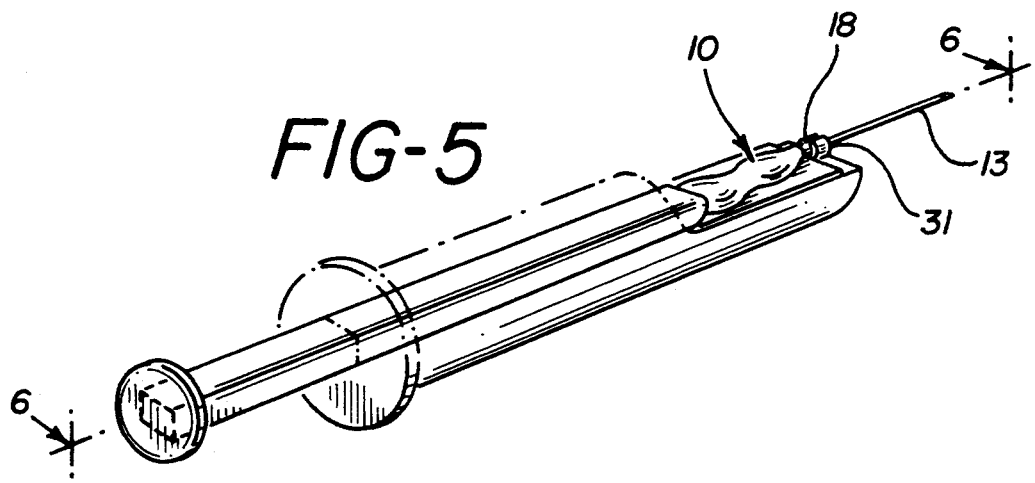
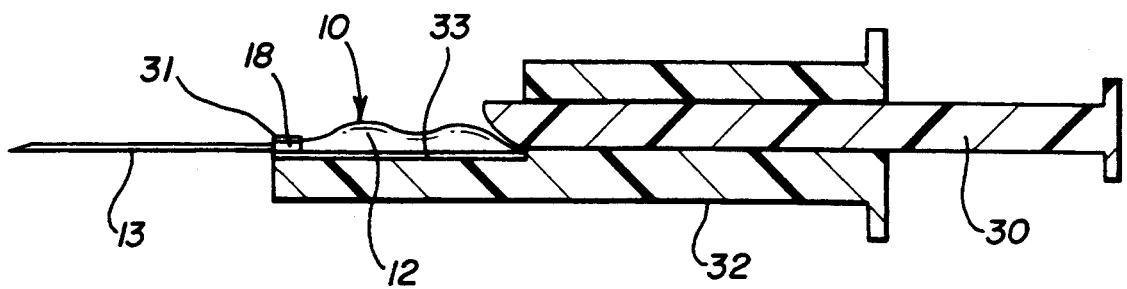

VACCINE DELIVERY SYSTEM

SUMMARY OF THE INVENTION

This invention relates to a vaccine delivery system wherein an aqueous vaccine diluted to human dosage concentration is loaded into a presterilized single dosage syringe, having a compressible "hour-glass" shaped container portion fitted with a needle, enclosed in a rigid clamp assembly having syringe-type activation means for compressing and expelling the vaccine contents into the vaccine. The advantage of the "hour-glass" shaped body is that the volume of the contents encased therein, relative to the volume of the container, can be calibrated so that the contents can be aspirated, and yet still deliver a precise predetermined quantity of vaccine. The upper portion of the "hour-glass" container can be sized so that it is entirely filled with the dose to be delivered, while only a minute amount is forced into the aspirate. The vaccine administrator can easily aspirate, not waste any vaccine, yet also readily visualize that the upper portion of the "hour-glass" is full, and then without changing the position of the hand, and also without "suck-back", insert the needle smoothly under the patient's skin and continue compression to eject the contents.

This invention relates to the delivery of vaccines. More particularly, it concerns novel methods and apparatus for packaging and dispensing vaccines of the type which are administered by injection through a needle.

In general, vaccine delivery has to satisfy different inconsistent goals. It is an object of this invention to provide a device which is relatively inexpensive, and has simpler internal parts than the usual hypodermic syringe, while still maintaining the standard procedures of a syringe. In mass vaccinations, personnel administering the vaccine, especially in so called "underdeveloped nations," are not trained, in the use of unusual devices or those which require unusual manipulations to inject the vaccine.

In addition, the usual mode of administration of any injection is to depress the hypodermic syringe slightly while holding the device in the needle upright, only enough to force all air out, and to have a "bubble" of the liquid contents portion form at the tip of the upright needle. This initial operation, which compresses and then forces air out through the needle, is termed "aspiration," and is one with which medical personnel are thoroughly familiar. Subsequent to aspiration, the syringe is inserted under the skin of the patient, followed by depression of the syringe to eject the contents.

It will be readily appreciated that this three-step process, which is an acquired motor skill, quickly becomes an ingrained habit of administering all injections. Because the volume of the aspirate is discarded, wastage is significant in the aggregate.

One key element of this invention is the "hour-glass" shape of the main body region of the container portion of the syringe. This "hour-glass" shape can be precisely designed so that its volume permits the syringe contents to be aspirated. As the syringe is held in the upright position with the needle at the top to be aspirated, the contents of the "hour-glass" will have a volume less than the capacity of the container so that an empty space (head space) will be at the top of the "hour-glass." As the operator pushes on the syringe plunger portion to aspirate, the contents are forced into the top of the "hour-glass." The lower portion has been designed so that its volume is equal to the air in the container the volume of the aspiration drop, 30–50 microliters in excess of the volume of the desired dose. Therefore, normal aspiration can be achieved.

An optional modification provides a "stop" in the plunger travel, so that aspiration does not have to depend on eye-hand coordination, but is automatic and consequently more precise. The user is allowed to aspirate, while the loss on aspiration is automatically controlled using this "stop" or similar mechanical means.

The operator can then, while still holding the device by the barrel and the plunger, insert the needle under the skin of the patient, further depressing the plunger to eject the contents. The totality of the manipulative procedure is within the standard experience of the vaccine administrator (user).

It is an object of this invention to prepare a delivery system for a vaccine or other injectable pharmaceutical composition, which is capable of being precisely loaded with a small volume of active vaccine material amounts, and subsequently aspirated and manipulated in the standard manner while minimizing wastage of contents.

The process of "aspiration" is an important and familiar one in injection delivery of many pharmaceutical compositions, including vaccines. It consists of a compression of the chamber containing the composition which forces out air in order to assure the administrator that the needle is open and that no air will be injected in the patient. The administrator then, while still holding the syringe without decompressing the contents, in order to prevent "suck-back," inserts the needle under the patient's skin and further compresses the contents, forcing them out into the injection site, while subcutaneous or intramuscular.

This aspiration process, while it is important and valuable to the administrator, obviously wastes a small amount of the pharmaceutical contents. While this is not always a problem, when mass vaccinations, especially of small children or infants is being accomplished, the aggregate total aspirate wastage is significant.

It is one of the anomales of modem vaccine delivery systems, especially when targeted to small doses over an entire population, that the cost of the delivery system becomes a significant proportion of the vaccination. Since these delivery devices are not intended to be reused, but are disposable, the materials of choice are plastic tubes, or bags, fined with a needle and a means for expelling the contents. Unfortunately, the least expensive thin plastic tubing has an elastic memory, as well as being deformable and non-rigid, so that "aspiration," is difficult. This present invention cures this deficit, in that the tubing is encased in a rigid clamp assembly thereby permitting the contents to be aspirated.

According to one aspect of the invention, there is provided a novel single dosage vaccine delivery system including a hypodermic syringe which comprises an "hour-glass" shaped disposable container portion, a needle portion, and a multi-use, rigid clamp assembly having syringe-type activating means for compressing and expelling the contents. The "hour-glass" shaped container portion is made of a thermoformable plastic film material (which is compatible with medication, such as PVC, polypropylene, or a PET/polyethylene laminate, as well as flexible and resilient at room temperature), filled with a single dose of aqueous vaccine diluted to a concentration suitable for human administration. The needle portion of the syringe is conventional and consists of a hollow sharp needle for injection. The rigid clamp assembly protects the body, while enabling standard manipulation to expel the contents. It may be made out of any type of the more rigid moldable plastics such as PVC, polypropylene, polyesters such as PET, Delrin or the like.

A major advantage of this system is that the container is disposable while the clamp can be used for 1000–10,000 operations. Cost savings over conventional devices are achieved without sacrificing familiar manipulations of more expensive injection systems.

The disposable container portion of the system described above can be held at a temperature of from about 0° C. to about −10° C., so that the active component does not lose its titer and the unit can be held for long periods of time in this state. To prepare the unit for use, one removes it from the low temperature storage chamber and allows it to come to room temperature. During this operation the vaccine returns to the fluid state, the plastic container recovers its flexibility and the unit is ready to be used for injection after enclosing in the clamp assembly.

The invention will be more readily understood on reading the following description with references to the accompanying drawings, in which: FIG. 1 is a longitudinal view of part of the container portion fitted with a needle. FIG. 2 is an elevational view of the device shown in FIG. 1. FIG. 3 is a longitudinal view of the needle fitting shown in FIG. 2. FIG. 4 is an elevational view of the rigid clamp assembly having syringe-type activation means. FIG. 5 is an elevational view of the complete vaccine delivery system, including the clamp assembly with the container and needle in place. FIG. 6 is a cross-sectional view taken along the plane indicated at 6—6 of FIG. 5 in the direction of the arrows.

DETAILED DESCRIPTION OF THE PREFERRED EMBODIMENTS

Figure 1:
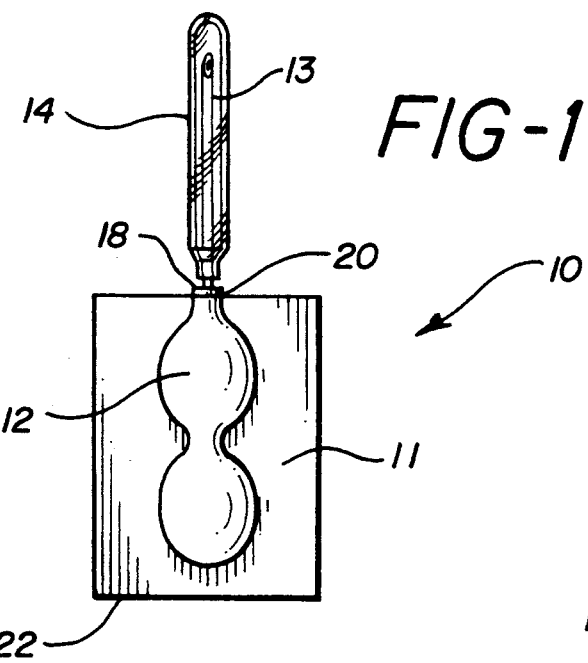
Figure 2:
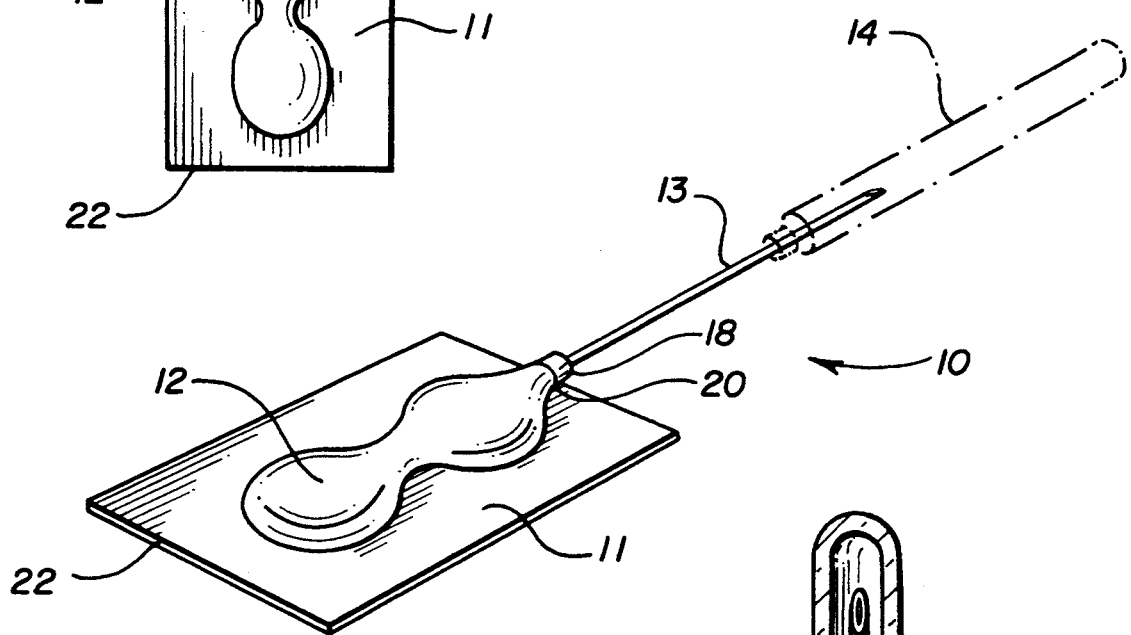

As can be seen in FIGS. 1 and 2, the syringe 10 comprises a compressible body portion 11, containing the "hour-glass" shaped body region 12 and a needle portion 13 and a dust guard 14. The container portion 11 is made of a soft plastic material which is resiliently flexible at room temperature. This material must be capable of remaining stable at very low temperatures, i.e. from about minus 10° C. to about −20° C. or below, and of recovering its resilient flexibility when returned to room temperature. Also, the material of the container portion 10 should be permeable to a gas sterilizing atmosphere such as ethylene oxide. Low density polyethylene has been found to be quite suitable for this purpose, although other plastics are equally useful.

The container portion 11 has a generally "hour-glass" shaped body region 12 which tapers inwardly at its upper end to a hollow cylindrical neck 18. A diaphragm 20 extends across the lower end of the neck 18 to close off the main body region. The lower end of the main body region is flattened and heat sealed closed as indicated at 22.

Figure 3:
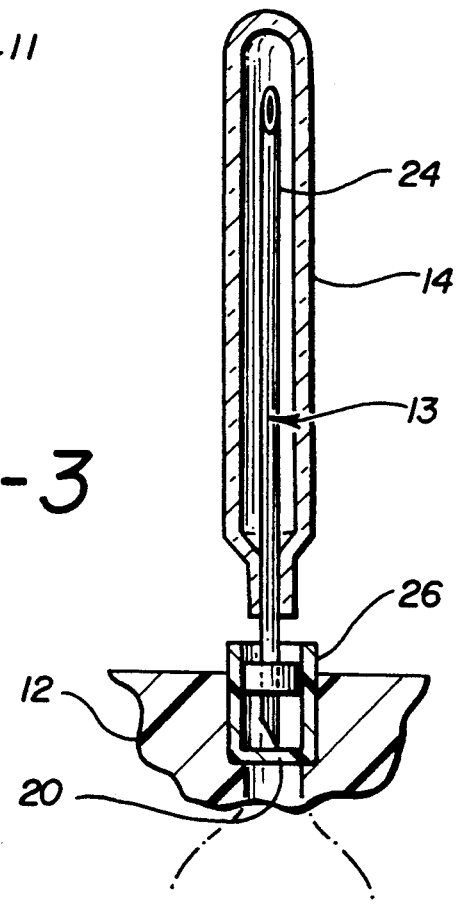

The needle portion 12 comprises a hollow elongated needle 24 which extends through, and is press fitted in a cap 26. The needle 24 is cut on a bias at both ends to form penetrating points; in the one case, for injection into a patient, and in the other case, for piercing the diaphragm 20. The collar 26 is dimensioned to fit snugly but slideably in the cylindrical neck 18 as illustrated in FIG. 3.

The dust guard 14 is molded of a plastic material, such as polyethylene, nylon or polypropylene, which may be somewhat harder than the material of the container portion 10. The dust guard 14 is also of generally tubular configuration and is closed at its upper end and open at its lower end.

The clamp assembly in FIG. 4 is formed of a rigid material such as moldable plastic including delrin and nylon, it has a plunger 30 which is slidable within a barrel 32. A flatted portion 33 is fitted with a snap collar 31.

In FIGS. 5 and 6, syringe 10 is placed on the flattened portion 33 of the clamp assembly, so that the snap collar 31 clamps around neck 18. To ready the syringe for an injection, the dust guard is pushed into the neck 18 to force the collar 26 and needle 24 downwardly until the lower end of the needle pierces the diaphragm 20 and opens into the main body region 12. After removal of the dust guard, the device can be aspirated and used. First, plunger 30 is pushed while holding in the usual needle up position, therefore depressing the lower portion of the body region 12, forcing out air to aspirate. The rigid clamp permits the needle to be easily inserted into the patient, and the comet injection administered.

The above described vaccine delivery system provides preloaded single dosage syringe units which are readily made usable for injection.

What is claimed is:

1. A vaccine delivery system suitable for human or animal administration comprising a single dosage hypodermic syringe having an "hour-glass" shaped container portion made of plastic, said container portion sized so that the air and the minor drop of contents ejected during aspiration is equivalent in volume to the lower half of the "hour-glass" shaped container; a needle portion comprising a hollow sharp needle extending from one neck of the plastic container portion and a rigid clamp assembly means fitted with plunger means at the other end which can be slidably moved over the container portion expel the container contents.

2. The system of claim 1 in which the container portion is disposable and made of a thermoformed plastic compatible with medication.

3. The system of claim 2 in which the container portion is made of PVC, polypropylene or PET/polyethylene laminate.

4. The system of claim 1 in which the rigid clamp assembly is multiuse and made of a moldable plastic.

5. The system of claim 4 which the clamp assembly is made of Delrin polyester.

6. The system of claim 5 in which the clamp assembly has a flat surface to receive the container portion, fitted on one end with a snap collar to engage the neck of the container portion and having plunger means at the other end.

* * * * *